United States Patent [19]
Richardson

[11] Patent Number: 5,846,488
[45] Date of Patent: Dec. 8, 1998

[54] FIELD KIT FOR DETECTING ANALYTES

[75] Inventor: John G. Richardson, Princeton, N.J.

[73] Assignee: Hawaii Chemtect International, Pasadena, Calif.

[21] Appl. No.: 883,213

[22] Filed: Jun. 26, 1997

Related U.S. Application Data

[63] Continuation of Ser. No. 774,061, Oct. 9, 1991, abandoned.

[51] Int. Cl.$^6$ ............................. G01N 33/50; B01L 11/00
[52] U.S. Cl. ........................... 422/61; 422/102; 435/810; 206/469; 206/569
[58] Field of Search ............................. 422/61, 102, 104; 436/808; 435/810; 206/469, 532, 569

[56] References Cited

U.S. PATENT DOCUMENTS

| | | |
|---|---|---|
| D. 262,095 | 12/1981 | Takahashi . |
| D. 268,167 | 3/1983 | Fox . |
| D. 282,243 | 1/1986 | Mason . |
| D. 342,031 | 12/1993 | Richardson . |
| 3,948,391 | 4/1976 | Beaman . |
| 3,967,730 | 7/1976 | Driscoll et al. . |
| 4,106,621 | 8/1978 | Sorenson . |
| 4,155,454 | 5/1979 | Ryden . |
| 4,236,636 | 12/1980 | Kuchenbecker . |
| 4,617,278 | 10/1986 | Reed . |
| 4,703,017 | 10/1987 | Campbell et al. . |
| 4,786,604 | 11/1988 | Michael . |
| 4,803,048 | 2/1989 | Nason . |
| 4,816,392 | 3/1989 | Hokama . |
| 5,028,535 | 7/1991 | Buechler et al. . |
| 5,067,611 | 11/1991 | Hagmann et al. . |
| 5,100,621 | 3/1992 | Berke et al. . |

OTHER PUBLICATIONS

Hokama, Y. "Simplified Solid–Phase Immunobead Assay for Detection of Ciguatoxin and Related Polyethers", J. Clin. Lab. Anal., 4(3), 213–17 (1990) Chemical Abstracts V. 114:22753.

"A Radioimmunoassay for the Detection of Ciguatoxin," by Y. Hokama, A.H. Banner and D.B. Boylan, *Toxicon*, 15:317–325 (1977).

"A Rapid Enzyme–Immunoassay for the Detection of Ciguatoxin in Contaminated Fish Tissues," by Y. Hokama, M.A. Abad and L.H. Kimura, *Toxicon*, 21:817–824 (1983).

"A Rapid, Simplified Enzyme Immunoassay Stick Test for the Detection of Ciguatoxin and Related Polyethers from Fish Tissues," by Yoshitsugi Hokama, *Toxicon*, 23(6):939–946 (1985).

"Assement of a Rapid Enzyme Immunoassay Stick Test for the Detection of Ciguatoxin and Related Polyether Toxins in Fish Tissues," by Y. Kokama, L.K. Iwanmoto, M.N. Kobayashi, C.S. Goto and L.K. Nakagawa, *Biol. Bull.*, 172:144–153 (Feb. 1987).

"Ciguatera Fish Poisoning" by Y. Kokama, *Journal of Clinical Analaysis*, 2:44–50 (1988).

"Monoclonal Antibody (Mab) in Detection of Ciguatoxin (CTX) and Related Polyethers by the Stick–Enzyme Immunoassay (S–EIA) in Fish Tissues Associated with Ciguatera Poisoning," by Y. Hokama, S.A.A. Honda, M.N. Kobayashi, L.K. Nakagawa, A.Y. Asahina and J.T. Miyauara, *Mycotoxins and Phycotoxins '88, A Collection of Invited Papers at the Seventh International IUPAC Symposium on Mycotoxins and Phcotoxins*, 303–310 (1989).

(List continued on next page.)

*Primary Examiner*—Jeffrey Snay
*Attorney, Agent, or Firm*—Lyon & Lyon LLP

[57] ABSTRACT

The present invention relates to a field kit for the detection of analytes and to a method for using such a field kit. The field kit comprises a tray and lid adhered to the surface of the tray. Reaction-reagent compartments are formed by recesses in the tray when the tray is adhered to the lid. Probe compartments may also be included if desired. In operation, the tray and lid are bent at a score line to open the wells containing the reaction reagents. The lid is bent to form an A-shaped structure so that the kit may be placed in an upright position for use. A portion of the lid is peeled back from the tray to release probes and other, non-liquid components, if present.

26 Claims, 2 Drawing Sheets

OTHER PUBLICATIONS

"The Latex Fixation Test, I. Applicatio to the Serlogic Diagnois of Rheumatoid Arthritis," Jacques M. Singer and Charles M. Plotz, *American Journal of Medicine*, pp. 888–892 (Dec., 1956).

"Simplified Solid–Phase Immunobead Assay for Detection of Ciquatoxin and Related Polyethers," by Yoshitsugi Hokama, *Journal of Clinical Laboratory Analysis*, 4:213–217 (Apr. 1990).

"Evaluation of the Stick Enzyme Immunoassay in *Cranx* sp. And *Seriola dumerili* Associated with Ciguatera," by Y. Hokama, A.Y. Asahina, T.W.P. Hong, E.S. Shang and J.T. Miyahara, *Journal of Clinical Laboratory Analysis*, 4:363–366 (Aug. 1990).

"Monoclonal Antibodies in the Detection of Ciquatoxin and Other Toxic Polyethers in Fish Tissues by a Rapid Poke Stick Test," by Y. Hokama, A.M. Osugi, S.A.A. Honda, M.K. Matsuo, *Proceedings of the Fifth International Coral Reef Congress*, 4:449–455 (1985).

FIELD KIT FOR DETECTING ANALYTES

This is a continuation of application Ser. No. 07/774,061 filed on Oct. 9, 1991 now abandoned.

FIELD OF THE INVENTION

This invention relates to a field kit for the detection of analytes.

BACKGROUND OF THE INVENTION

Increasing concerns of the pollution of the environment has led to the need for the general public to be able to test the food and the water they drink for the presence of toxins and contaminants. This need is especially important when the food or the water has not been tested by governmental authorities; for example, fish caught by sports fisherman, or water which might be drunk on camping trips. Also, there is often a desire to test food and water when traveling in countries where quality control of contamination may not be as rigorous as required by the consumer. Another circumstance where such testing is desired is after a disaster, such as a flood or an earthquake, when contamination of water and food is common.

Testing methods are available for the detection of analytes, such as toxins and other contaminants. However, these testing methods are often complicated and are not easily conducted by a lay person.

Therefore, there is a need for an easy-to-use field kit to test for analytes, such as toxins and other contaminants of food. It is also desirable that such a field kit be inexpensive and have the ability to be stored for extended periods of time.

SUMMARY OF THE INVENTION

The present invention relates to a field kit for detecting analytes and to a method for using such a field kit.

The field kit comprises a tray and a lid adhered to the surface of the tray. Reagent compartments are formed by recesses in the tray when it is adhered to the lid. Other compartments may be added if desired to contain other assay components as required.

In operation, the lid and tray are bent to open reagent wells and to form an A-shaped stand, structured so that the kit may be placed in a free-standing, upright position for use. Other assay components, if present, are released by peeling back a portion of the lid.

DESCRIPTION OF THE DRAWINGS

These features and advantages of the invention, as well as other features and advantages of the invention, will be more apparent from a reading of the claims and of the detailed description of the invention in conjunction with the drawings described below.

DETAILED DESCRIPTION

The present invention relates to a field kit for the detection of analytes and to a method for using the field kit.

Figure 1:
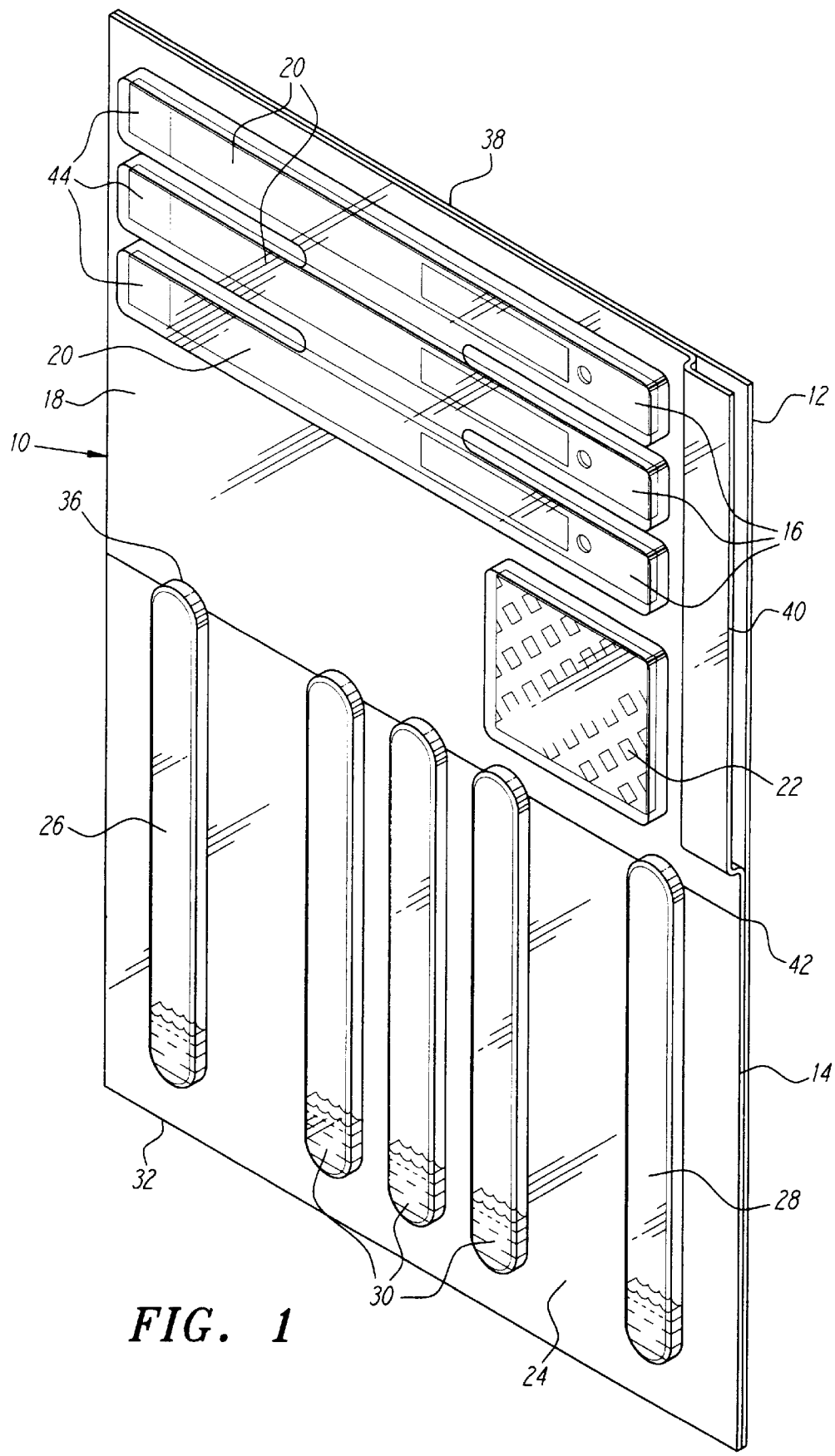
FIG. 1 is a front perspective view of a field kit for the detection of analytes.

FIG. 1 shows a field kit 10. The field kit comprises a lid 12 which is made from a rigid-but-bendable, non-porous material, such as a laminated material comprising one or more layers selected from the group consisting of plastic, paper, foil and adhesive. It is preferable that it be coated with a water-resistant material, such as foil or plastic, to prevent liquids contained in the reagent compartments from penetrating the lid material and evaporating or being contaminated by the lid material or the environment. The coating material also allows a tray 14 to be readily removed without tearing the lid material.

The tray is adhered to the surface of the lid by an adhesive such as that supplied by Rolling Packaging Products, Inc. (Catalog No. 26-1045). The tray is preferably made from transparent plastic or other suitable material so that the contents of the kit can be observed while the kit is in use. The tray is molded to contain a plurality of recesses so that, when the tray is adhered to the lid, a plurality of individual compartments are formed between the lid and the tray. The surface of the tray, between the recesses, is adhered to the surface of the lid to form individual, sealed compartments.

In one embodiment of the present invention, recesses 16, located on an upper half of the lid 18, form compartments for holding probes 20, i.e., the probe compartments. The probes are used for dipping into the material to be tested, to bind the analyte being assayed. In some cases, e.g., where water is being tested, such probes may not be required, and the material being tested can be transferred directly to the assay reagents. In such cases where a liquid is being transferred, it is desirable to include a dropper in a compartment in the kit.

Probes typically comprise positive and negative control probes and test probes. The positive control probes are probes that have been exposed to the analyte to be tested, or to an analog of the analyte, so that, when the probe is reacted with the reaction reagents, a positive result will be obtained. Negative control probes are probes that have not been exposed to the analyte to be tested, or to an analog of the analyte, so that, when they are reacted with the reaction reagents, a negative result will be obtained. Test probes are probes that are to be exposed to a potential source of an analyte such as water or food. The test probes, after reacting with the reaction reagents, are compared with the negative and positive controls to determine if a positive or a negative result has been obtained and, therefore, if the food or water is contaminated with the analyte being tested.

In the case of water, other liquids, or other tests where a probe is not used, positive and negative controls may be provided in the kit as a liquid or in another suitable form in separate compartments. These compartments are opened and added to reaction-reagent compartments at the time of assaying a test sample. Alternatively,. where the reaction products are sufficiently stable, it may be desirable to provide in the kit prereacted positive and negative controls in separate compartments.

An additional recess 22, a blotter compartment, may be located on the upper half of the tray for holding blotting material, such as paper toweling or other suitable material.

Recesses located on the lower half of the tray 24 form sealed compartments for holding and isolating reaction reagents. In one embodiment, where fixation of the analyte to the probe is required, one compartment 26 (the fixative compartment or well) contains a fixative reagent. Where washing of the probes is required, after they have been reacted with the reaction reagents, there is provided another compartment 28 (the wash compartment or well), which contains a wash solution. Other compartments 30 (reagent compartments or wells) each contain reaction reagents. The reaction reagents may be in the form of a solution or may be dried or lyophilized and reconstituted, prior to use. In the case where the reaction reagents are to be reconstituted, the reconstitution solution is also provided in a well in the field kit. Where such transfer of a liquid is desirable, a means for transferring the liquid, such as a dropper, may be provided in a separate compartment.

The reagent wells are parallel to each other, and each runs from the lower edge 32 of the tray to positions 36, located about midway between the lower edge 32 and the upper edge 38 of the lid, and extending from the lower edge to beyond score line 42.

Also molded into the tray, at an edge of the upper half of the lid, is a recess. This recess is open at the edge and provides a tab 40, or means of grasping the tray, so that the upper half of the tray can be peeled back from the lid to release the probes and the blotter from their compartments. The score line 42 is located on the lid and tray and is perpendicular to the longitudinal axis of the reaction-reagent compartments on the lower half of the tray. The score is located so that, when the tray and lid are bent at the score line, the reaction-reagent wells, or wells containing other liquid components, are open at their upper end 36.

Figure 2:
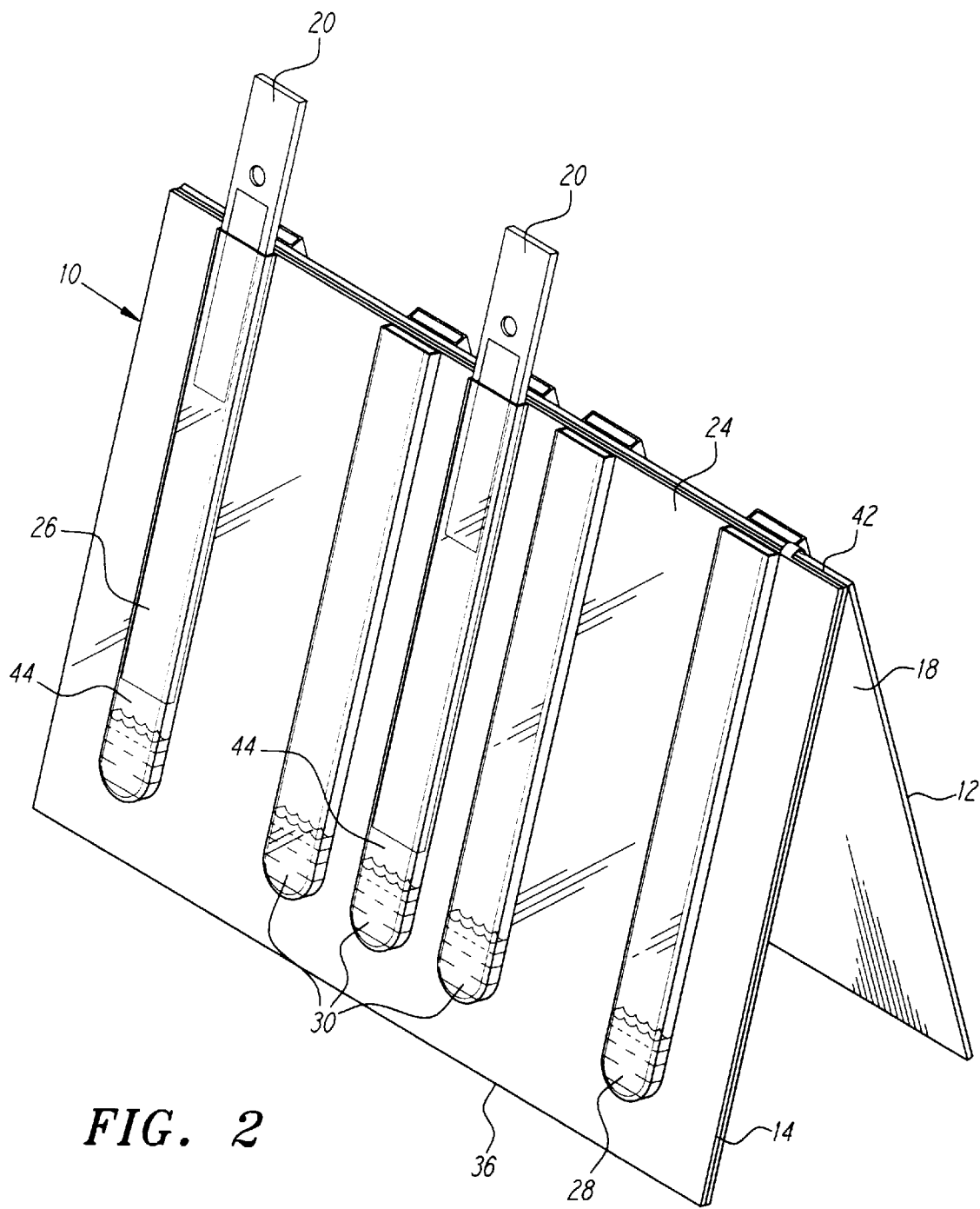
FIG. 2 is a front perspective view of an in-use field kit for the detection of analytes.

The lid also has a score line at the same location as the score line of the tray. The score line on the lid allows the lid to be bent, approximately in half, to form an A-shaped structure, so that the kit will stand upright in use, with edges 32 and 38 resting on a flat surface and score line 42 forming the apex of the "A", as shown in FIG. 2.

In order for one to use the field kit, the kit is held in an upright position so that the liquids, or dried powders, in wells 24, 26, and 30 fall to the bottom of the wells, located near edge 32. The kit may be tapped against a solid surface to ensure all the contents of the wells are at the bottom of the wells. The kit is then opened by grasping tab 40 and peeling the top half of the lid 18 from the tray. Peeling away the upper half of the lid allows for the removal of the probes and the blotter from their compartments. The lid and tray are then bent at the score line 42, to open the reaction-reagent compartments and to form an A-shaped structure, which can be placed on a surface, to stand on edges 32 and 38, with the score line forming the apex of the "A", and which results in the reagent-containing wells being placed in an upright position.

The above descriptions of exemplary embodiments of a kit for detecting analytes and of a method for using such a kit, are for illustrative purposes. Because of variations which will be apparent to those skilled in the art, the present invention is not intended to be limited to the particular embodiments described above. The present invention may also be practiced in the absence of any element not specifically disclosed. The scope of the invention is defined by the following claims.

What is claimed is:

1. A field kit for the detection of an analyte comprising:
   a lid;
   a tray adhered to the top surface of said lid, said tray comprising (a) means releaseably containing probes and (b) means separately containing a plurality of reaction reagents, said means separately containing said plurality of reaction reagents being separate from said means containing probes; and
   a score-line located in the surface of said tray enabling bending of said tray such that the kit will stand upright when in use;
   wherein said score-line passes through said reagent containing means such that the reagent containing means is opened when said tray is bent along said score line; and
   wherein one or more of said probes is receivable within said reagent containing means when the reagent containing means is opened.

2. The field kit recited in claim 1 wherein said means containing probes comprises one or more recesses that forms one or more probe compartments between said lid and said tray.

3. The field kit recited in claim 2 wherein at least one of said probe compartments is sealed to prevent contamination from entering.

4. The field kit recited in claim 2 wherein said lid comprises a first portion and a second portion, said first portion being adhered to said top surface of said tray and being peelably removable from said tray so as to expose the probes contained therein.

5. The field kit recited in claim 1 wherein said means separately containing a plurality of reaction reagents comprises a plurality of recesses that forms a plurality of reaction reagent compartments between said lid and said tray.

6. The field kit recited in claim 5 wherein said reaction reagent compartments are comprised of material that is impervious to the reaction reagents contained therein.

7. The field kit recited in claim 5 wherein said reaction reagent compartments are sealed to prevent evaporation of the reaction reagents contained therein.

8. The field kit recited in claim 5 wherein said score-line passes through one or more of said reaction reagent compartments so that when said tray is bent along said score-line one or more of said reaction reagent compartments is opened.

9. The field kit recited in claim 5 wherein said reaction reagent compartments contain at least some liquid reaction reagent.

10. The field kit recited in claim 5 wherein said reaction reagent compartments contain at least some solid reaction reagent.

11. The field kit recited in claim 1 wherein said tray is comprised of a transparent and moldable material.

12. The field kit recited in claim 1 wherein said tray further comprises a means for grasping said tray in order to peel a portion of said lid from said tray.

13. The field kit recited in claim 11 further comprising means for containing blotters, wherein said means for containing blotters is separate from said for separately containing a plurality of reaction reagents.

14. The field kit recited in claim 11 wherein said lid comprises a first portion and second portion adhered to said tray, said first portion overlies said means containing probes and is peelably removable from said tray so as to expose the probes contained in said means containing probes.

15. A field kit for the detection of an analyte comprising:
   a lid having a first portion and a second portion;
   a tray adhered to said first portion and said second portion of said lid;
   a probe compartment positioned between said lid and said tray;
   a plurality of probes releasably contained within said probe compartment;
   a plurality of distinct reaction reagent compartments containing reaction reagents and positioned between said lid and said tray and separated from said probe compartment;
   a score-line located in said tray such that when said tray is bent along said scoreline at least one of said reaction reagent compartments is opened
   wherein one or more of said probes is receivable within one of said reagent compartments when the reagent compartments are opened.

16. The field kit recited in claim 5 wherein said means containing probes comprises one or more recesses that forms one or more probe compartments between said lid and said tray.

17. The field kit recited in claim 6 wherein said means containing probes comprises one or more recesses that forms one or more probe compartments between said lid and said tray.

18. The field kit recited in claim 7 wherein said means containing probes comprises one or more recesses that forms one or more probe compartments between said lid and said tray.

19. The field kit recited in claim 8 wherein said means containing probes comprises one or more recesses that forms one or more probe compartments between said lid and said tray.

20. The field kit recited in claim 9 wherein said means containing probes comprises one or more recesses that forms one or more probe compartments between said lid and said tray.

21. The field kit recited in claim 10 wherein said means containing probes comprises one or more recesses that forms one or more probe compartments between said lid and said tray.

22. The field kit recited in claim 15 further comprising a blotter compartment positioned between said lid and said tray and separate from said plurality of distinct reaction reagent compartments.

23. The field kit recited in claim 15 wherein said reaction reagent compartments are formed of material that is impervious to the reaction reagent that it contains.

24. The field kit recited in claim 23 wherein said tray is formed of material that is moldable.

25. The field kit recited in claim 15 wherein said tray is formed of material that is transparent.

26. The field kit recited in claim 15 wherein said field kit further comprises a tab to permit selective separation of said first portion of said lid from said tray.

* * * * *

UNITED STATES PATENT AND TRADEMARK OFFICE
CERTIFICATE OF CORRECTION

PATENT NO. : 5,846,488

DATED : December 8, 1998

INVENTOR(S) : John G. Richardson

It is certified that error appears in the above-identified patent and that said Letters Patent is hereby corrected as shown below:

Col. 4, line 42, "11" should read -- 1 --.
Col. 4, line 44, "for" should read -- means --.
Col. 4, line 46, "11" should read -- 1 --.
Col. 4, line 64, "scoreline" should read -- score-line --.
Col. 4, line 65, "opened" should read --opened; --.

Col. 6, insert after claim 26 the following claims:

-- 27. The field kit recited in claim 15 wherein said first portion of said lid overlies said probe compartment and is peelably removable from said tray so as to expose the probes contained in said probe compartment.

28. The field kit recited in claim 15 wherein said probe compartment is sealed by said adherence between said tray and said first portion of said lid.

29. The field kit recited in claim 15 wherein said reaction reagent compartments are sealed from one another by said adherence between said tray and said lid.

30. The field kid recited in claim 29 wherein said reaction reagent compartments are sealed from one another by said adherence between said tray and said second portion of said lid--.

UNITED STATES PATENT AND TRADEMARK OFFICE
CERTIFICATE OF CORRECTION

PATENT NO. : 5,846,488
DATED : December 8,1998
INVENTOR(S) : John G. Richardson

It is certified that error appears in the above-identified patent and that said Letters Patent is hereby corrected as shown below:

31. The field kit recited in claim 15 wherein said plurality of distinct reaction reagent compartments contains at least some liquid reaction reagent.

32. The field kit recited in claim 15 wherein said plurality of distinct reaction reagent compartments contains at least some solid reaction reagent. --

Signed and Sealed this

Twenty-ninth Day of June, 1999

Attest:

Q. TODD DICKINSON

*Attesting Officer*   Acting Commissioner of Patents and Trademarks